United States Patent [19]

Kershner

[11] Patent Number: 4,465,837

[45] Date of Patent: Aug. 14, 1984

[54] PREPARATION OF 5-METHYL-2-OXAZOLIDINONES

[75] Inventor: Larry D. Kershner, Midland, Mich.

[73] Assignee: The Dow Chemical Company, Midland, Mich.

[21] Appl. No.: 384,813

[22] Filed: Jun. 3, 1982

[51] Int. Cl.$^3$ ............................................ C07D 263/04
[52] U.S. Cl. .................................... 548/229; 549/449; 564/32
[58] Field of Search ......................... 548/229; 549/229

[56] References Cited

U.S. PATENT DOCUMENTS 4,281,200  7/1981  Snoble ................................. 548/229

FOREIGN PATENT DOCUMENTS 1414820  11/1975  United Kingdom ................ 549/449

Primary Examiner—Donald G. Daus
Assistant Examiner—S. A. Gibson
Attorney, Agent, or Firm—Douglas N. Deline

[57] ABSTRACT

5-Methyl-2-oxazolidinone and 5-methyl-3-(2-hydroxypropyl)-2-oxazolidinone are prepared by contacting urea and propylene carbonate in the presence of an initiator at a temperature from about 120° C. to about 200° C.

6 Claims, No Drawings

PREPARATION OF 5-METHYL-2-OXAZOLIDINONES

BACKGROUND OF THE INVENTION

The present invention relates to the production of 5-methyl-2-oxazolidinones. More particularly, the present invention concerns a method for preparing 5-methyl-2-oxazolidinones in high yields and selectivities by the reaction of urea with propylene carbonate.

In U.S. Pat. No. 3,133,932, 2-oxazolidinones are prepared by the thermal decomposition of β-hydroxyethylurea or substituted β-hydroxyethylureas which in turn may be prepared by the reaction of urea and ethanolamines or a substituted ethanolamine.

SUMMARY OF THE INVENTION

According to the present invention process, propylene carbonate is contacted with urea at an elevated temperature to prepare 5-methyl-2-oxazolidinone and optionally 3-(2-hydroxypropyl)-5-methyl-2-oxazolidinone. A catalytically effective amount of an initiator may be employed to aid in the rate of reaction if desired.

The reaction may be employed as part of a multistep preparation of isopropanolamines from ammonia and propylene carbonate. Accordingly, urea may be prepared by the reaction of propylene carbonate or other alkylene carbonates with ammonia. In addition the 5-methyl-2-oxazolidinone or 3-(2-hydroxypropyl)-5-methyl-2-oxazolidinone reaction products of the instant process may be readily hydrolyzed to form monoisopropanolamine or diisopropanolamine. It may be seen that the process allows the artisan to selectively prepare monoisopropanolamine and diisopropanolamine while preparing substantially none of the higher molecular weight triisopropanolamine.

DETAILED DESCRIPTION OF THE INVENTION

Both starting reactants, propylene carbonate and urea are well-known compounds that are commercially available or easily prepared by known methods. For example, preparation of urea by the reaction of alkylene carbonates such as ethylene carbonate with ammonia in the gas phase at temperatures of about 50° C.–150° C. and pressures of about 30–45 atmospheres is already known, having been described in British Pat. No. 1,414,820. Or course, urea from any source may be employed according to the instant process.

The two reactants are combined at elevated temperatures and pressures in order to prepare the desired condensation products according to the following schematic illustration:

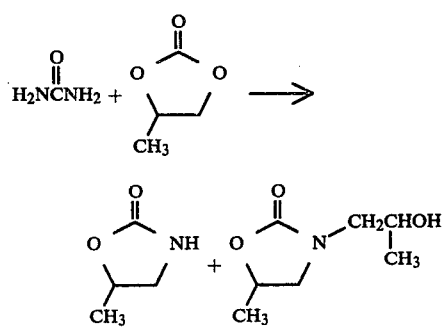

Suitable temperatures for the reaction are from about 120° C. to about 200° C., preferably from about 140° C. to about 180° C. and most preferably about 160° C. At temperatures less than about 120° C., essentially no reaction occurs. At elevated temperatures greater than about 200° C., by-products such as substituted ureas may be formed.

The reaction may be conducted at reduced or elevated pressures. However, because of the formation of by-products $CO_2$ and $NH_3$, elevated pressures are not preferred. The course of the reaction is aided by removal of gaseous products as formed. For this purpose a sweep gas of nitrogen or other inert gas may be employed, if desired.

The reaction is aided by the presence of a small but effective amount of an initiator. Suitable initiators include bases such as alkali metal alkoxides or hydroxides, salts of strong bases and weak acids such as sodium carbonate, and non-nucleophilic organic bases. The latter class comprises in practice either aliphatic or aromatic tertiary amines.

Additional suitable initiators are the well-known quaternary salts such as ammonium or phosphonium salts having inert counterions. Preferred are such salts of the formula $R_4AY$ where each R is a hydrocarbon moiety, A is a quaternary nitrogen or phosphorus atom and Y is an inert counterion such as chloride, bromide, fluoride, bicarbonate, sulfate, formate, acetate, benzoate, phenate and the like. Suitable R groups include alkyl, aryl, cycloalkyl, etc., of up to about 10 carbons. Also two R groups may together with A form a heterocyclic ring such as pyridine.

A further class of initiators include alkali metal halide salts, optionally in the presence of a solubilizing agent such as a crown ether.

Preferred initiators are the alkali metal carbonates such as sodium carbonate. The initiator is added in an amount from about 0.01 percent to about 10 percent by weight.

The reaction is conducted in reactors of ordinary design and construction. Suitably, the reactor may be comprised of glass, steel, glass lined steel, nickel, stainless steel, etc.

The reactants and initiator are contacted and heated to the desired reaction temperature, preferably while stirring the reaction mixture. Reaction is continued until the desired degree of completion is reached. Reaction times may vary from about one hour to about 15 hours or more and are influenced by the temperature of the reaction.

The ratio of reactants may be varied to increase or decrease the relative proportions of monoisopropanolamine to diisopropanolamine prepared. Generally about a 1:1 molar ratio of propylene carbonate to urea will give increased levels of monoisopropanolamine, whereas molar ratios of about 2:1 tend to produce larger amounts of diisopropanolamine.

Once the desired degree of conversion of starting reactants is obtained, the reaction is terminated and the 2-oxazolidinone products recovered. Purification if desired may be accomplished by ordinary techniques such as distillation.

As previously mentioned, the 2-oxazolidinone reaction products may be further hydrolyzed to prepare monoisopropanolamine and diisopropanolamine products. The hydrolysis may be easily accomplished by heating in the presence of aqueous caustic or other strong base. Suitable temperatures are from about 50° C.

to reflux temperature. At least two moles of caustic for each mole of propylene carbonate originally employed are required. Monoisopropanolamine is prepared by hydrolysis of 5-methyl-2-oxazolidinone while diisopropanolamine is prepared by hydrolysis of 5-methyl-3-(2-hydroxypropyl)-2-oxazolidinone. It is therefore seen that selective formation of the desired end product may be easily controlled by merely changing the initial ratio of propylene carbonate to urea of the invented process.

The present invention is considered unique and surprising inasmuch as attempts to prepare similar reaction products of ethylene carbonate and urea have not resulted in preparation of significant quantities of 2-oxazolidinone but rather primarily resulted in formation of ethyleneurea or hydroxyethylurea.

SPECIFIC EMBODIMENTS

Having described the invention, the following examples are included as further illustrative of the present invention and are not to be construed as limiting.

EXAMPLE 1

Urea (12.0 g, 0.2 mole), propylene carbonate (20.4 g, 0.2 mole) and potassium carbonate (0.32 g) were combined in a 50-ml glass flask equipped with a stirrer, heating mantle, condenser and thermocouple. A bubbler was attached to the exit of the condenser. The reactants were heated to 160° C. while stirring. After about 7½ hours evolution of carbon dioxide ceased. The liquid product weighed 17.0 g and was analyzed to show by weight 5-methyl-2-oxazolidinone-59.3 percent, 5-methyl-3-(2-hydroxypropyl)-2-oxazolidinone-5.2 percent, propylene glycol-1.1 percent and propylene carbonate reactant-0.6 percent. In addition, about 8.3 g of solid ammonium carbonate had sublimed inside the condenser.

EXAMPLE 2

The reaction conditions of Example 1 were substantially repeated except that about a 2:1 molar ratio of propylene carbonate to urea was employed. After reaction for about 5 hours at about 160° C., the percent conversion of propylene carbonate was about 99.5 percent. Selectivity to 5-methyl-2-oxazolidinone was 28.2 percent, while selectivity to 5-methyl-3-(2-hydroxypropyl)-2-oxazolidinone was about 50.0 percent.

EXAMPLE 3

The reaction product of Example 1 was hydrolyzed. Accordingly, 6.0 g of the liquid product mixture was combined with NaOH (6.0 g) and water (10 ml) and heated for 3 hours at 95° C. in the same reaction flask initially employed. After cooling, sodium carbonate (8.0 g) was removed by filtration and 15.1 g of a liquid product recovered. Analysis showed a mixture of products comprising 31.5 percent by weight monoisopropanolamine, 0.5 percent diisopropanolamine and 0.7 percent propylene glycol.

What is claimed is:

1. A process for preparing 5-methyl-2-oxazolidinone, 5-methyl-3-(2-hydroxypropyl)-2-oxazolidinone or mixtures thereof, comprising contacting urea and propylene carbonate in the presence of an initiator at a temperature of from about 120° C. to about 200° C.

2. The process of claim 1 wherein the temperature is from about 140° C. to about 180° C.

3. The process of claim 2 wherein the temperature is about 160° C.

4. The process of claim 1 wherein the molar ratio of propylene carbonate to urea is from about 1:1 to about 2:1.

5. The process of claim 1 wherein the initiator is selected from the group consisting of bases, salts of strong bases and weak acids, non-nucleophilic organic bases, quaternary salts, and alkali metal halides.

6. The process of claim 5 wherein the initiator is an alkali metal carbonate.

* * * * *